US011540707B2

(12) United States Patent
Suyama et al.

(10) Patent No.: US 11,540,707 B2
(45) Date of Patent: Jan. 3, 2023

(54) ENDOSCOPE AND IMAGE PICKUP MODULE

(71) Applicant: OLYMPUS CORPORATION, Tokyo (JP)

(72) Inventors: Takuro Suyama, Ina (JP); Takatoshi Igarashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 548 days.

(21) Appl. No.: 16/662,362

(22) Filed: Oct. 24, 2019

(65) Prior Publication Data

US 2020/0058693 A1 Feb. 20, 2020

Related U.S. Application Data

(63) Continuation of application No. PCT/JP2017/016346, filed on Apr. 25, 2017.

(51) Int. Cl.
*A61B 1/05* (2006.01)
*A61B 1/00* (2006.01)
(Continued)

(52) U.S. Cl.
CPC .......... *A61B 1/051* (2013.01); *A61B 1/00018* (2013.01); *A61B 1/00114* (2013.01);
(Continued)

(58) Field of Classification Search
CPC ............ A61B 1/00009; A61B 1/00018; A61B 1/00096; A61B 1/00114; A61B 1/05;
(Continued)

(56) References Cited

U.S. PATENT DOCUMENTS 5,797,837 A * 8/1998 Minami ................. A61B 1/051
600/109
2005/0040509 A1 2/2005 Kikuchi et al.
(Continued)

FOREIGN PATENT DOCUMENTS

JP H08153820 A * 11/1994
JP 08-153820 A 6/1996
(Continued)

OTHER PUBLICATIONS

International Search Report dated Aug. 1, 2017 received in PCT/JP2017/016346.

*Primary Examiner* — Michael J Carey
*Assistant Examiner* — Julianna J Nicolaus
(74) *Attorney, Agent, or Firm* — Scully, Scott, Murphy & Presser, P.C.

(57) ABSTRACT

An endoscope includes an image pickup module, and the image pickup module includes: an image pickup device an external electrode being disposed on a back surface of the image pickup device; a wiring element provided with a through-hole passing through a first main surface and a second main surface, a first electrode on the first main surface being bonded with the external electrode; a signal cable bonded with a second electrode on the second main surface of the wiring element; and a first resin that seals a first bump bonding the first electrode and the external electrode and a second bump bonding the second electrode and the signal cable, and fills the through-hole.

6 Claims, 7 Drawing Sheets

(51) Int. Cl.
*H01L 23/00* (2006.01)
*H01L 27/146* (2006.01)

(52) U.S. Cl.
CPC ............... *A61B 1/05* (2013.01); *H01L 24/32* (2013.01); *H01L 24/73* (2013.01); *H01L 27/14618* (2013.01); *H01L 2224/3224* (2013.01); *H01L 2224/73204* (2013.01)

(58) Field of Classification Search
CPC ............ A61B 1/07; H01L 2224/73204; H01L 2224/92125
See application file for complete search history.

(56) References Cited

U.S. PATENT DOCUMENTS

| | | | | |
|---|---|---|---|---|
| 2007/0019952 | A1* | 1/2007 | Fujimori | H04N 5/2254 |
| | | | | 257/E31.118 |
| 2011/0249106 | A1* | 10/2011 | Makino | H05K 1/189 |
| | | | | 29/829 |
| 2015/0085094 | A1* | 3/2015 | Fujimori | H01L 27/14618 |
| | | | | 348/294 |

FOREIGN PATENT DOCUMENTS

| | | | | |
|---|---|---|---|---|
| JP | 09-326408 | A | 12/1997 | |
| JP | 2000-0232957 | A1 | 8/2000 | |
| JP | 2004-363289 | A | 12/2004 | |
| JP | 2012-064883 | A | 3/2012 | |
| JP | 2014-133046 | A | 7/2014 | |
| JP | 2014-188170 | A | 10/2014 | |
| JP | 2014188170 | A * | 10/2014 | ........... A61B 1/0008 |
| WO | 2014/156149 | A1 | 10/2014 | |

* cited by examiner

ENDOSCOPE AND IMAGE PICKUP MODULE

CROSS REFERENCE TO RELATED APPLICATION

This application is a continuation application of PCT/JP2017/016346 filed on Apr. 25, 2017, the entire contents of which are incorporated herein by this reference.

BACKGROUND OF INVENTION

1. Field of the Invention

The present invention relates to an endoscope configured to transmit, by a signal cable, an image pickup signal outputted by an image pickup module disposed at a distal end portion of an insertion portion and sealed with a resin at a bond portion, and the image pickup module sealed with the resin at the bond portion.

2. Description of the Related Art

An image pickup module including an image pickup device is used by being disposed at a distal end portion of an endoscope, for example.

A medical endoscope is sterilized after use by using a chemical or raising a temperature. Therefore, a bond portion of an image pickup module is protected by being covered with a resin when manufactured. On the other hand, in order to reduce invasion of the endoscope, miniaturization of the image pickup module is an important problem. The image pickup module for endoscope is ultra-small so that a maximum external dimension in an optical axis orthogonal direction is 1 mm or smaller for example. Thus, a process which is easy when manufacturing a relatively large image pickup module is sometimes difficult when manufacturing an image pickup module for endoscope.

Japanese Patent Application Laid-Open Publication No. 2014-133046 discloses an image pickup apparatus in which a bond portion of an image pickup device and a wiring board and a bond portion of the wiring board and a cable are sealed with the same resin.

SUMMARY OF THE INVENTION

An endoscope is configured to transmit, by a signal cable, an image pickup signal outputted by an image pickup module disposed at a distal end portion of an insertion portion, and the image pickup module includes: an image pickup device that includes a light receiving surface and a back surface, an external electrode being disposed on the back surface; a wiring element that includes a first main surface and a second main surface and is provided with a through-hole passing through the first main surface and the second main surface, a first electrode being disposed on the first main surface, a second electrode being disposed on the second main surface, and the first electrode being bonded with the external electrode of the image pickup device; the signal cable bonded with the second electrode of the wiring element; and a first resin that seals a first bond portion bonding the first electrode and the external electrode and a second bond portion bonding the second electrode and the signal cable, and fills the through-hole.

An endoscope of another embodiment is the endoscope configured to transmit, by a signal cable, an image pickup signal outputted by an image pickup module disposed at a distal end portion of an insertion portion, and the image pickup module includes: an image pickup device that includes a light receiving surface and a back surface, an external electrode being disposed on the back surface; a wiring element that includes a first main surface and a second main surface, a first electrode being disposed on the first main surface, a second electrode being disposed on the second main surface, and the first electrode being bonded with the external electrode of the image pickup device; the signal cable bonded with the second electrode of the wiring element; a first resin that seals a second bond portion of the second electrode and the signal cable; and a second resin that covers the first resin, a Young's modulus of the second resin being smaller than a Young's modulus of the first resin. A recessed portion is provided on the second main surface of the wiring element, the second electrode being disposed on an inner surface of the recessed portion, and the first resin is disposed only in the recessed portion.

An image pickup module of another embodiment includes: an image pickup device that includes a light receiving surface and a back surface, an external electrode being disposed on the back surface; a wiring element that includes a first main surface and a second main surface and is provided with a through-hole passing through the first main surface and the second main surface, a first electrode being disposed on the first main surface, a second electrode being disposed on the second main surface, and the first electrode being bonded with the external electrode of the image pickup device; a signal cable bonded with the second electrode of the wiring element; and a first resin that seals a first bond portion bonding the first electrode and the external electrode and a second bond portion bonding the second electrode and the signal cable, and fills the through-hole, and an interval between the back surface and the first main surface is smaller than an internal dimension of the through-hole.

DETAILED DESCRIPTION OF THE PREFERRED EMBODIMENT(S)

First Embodiment

Figure 1:
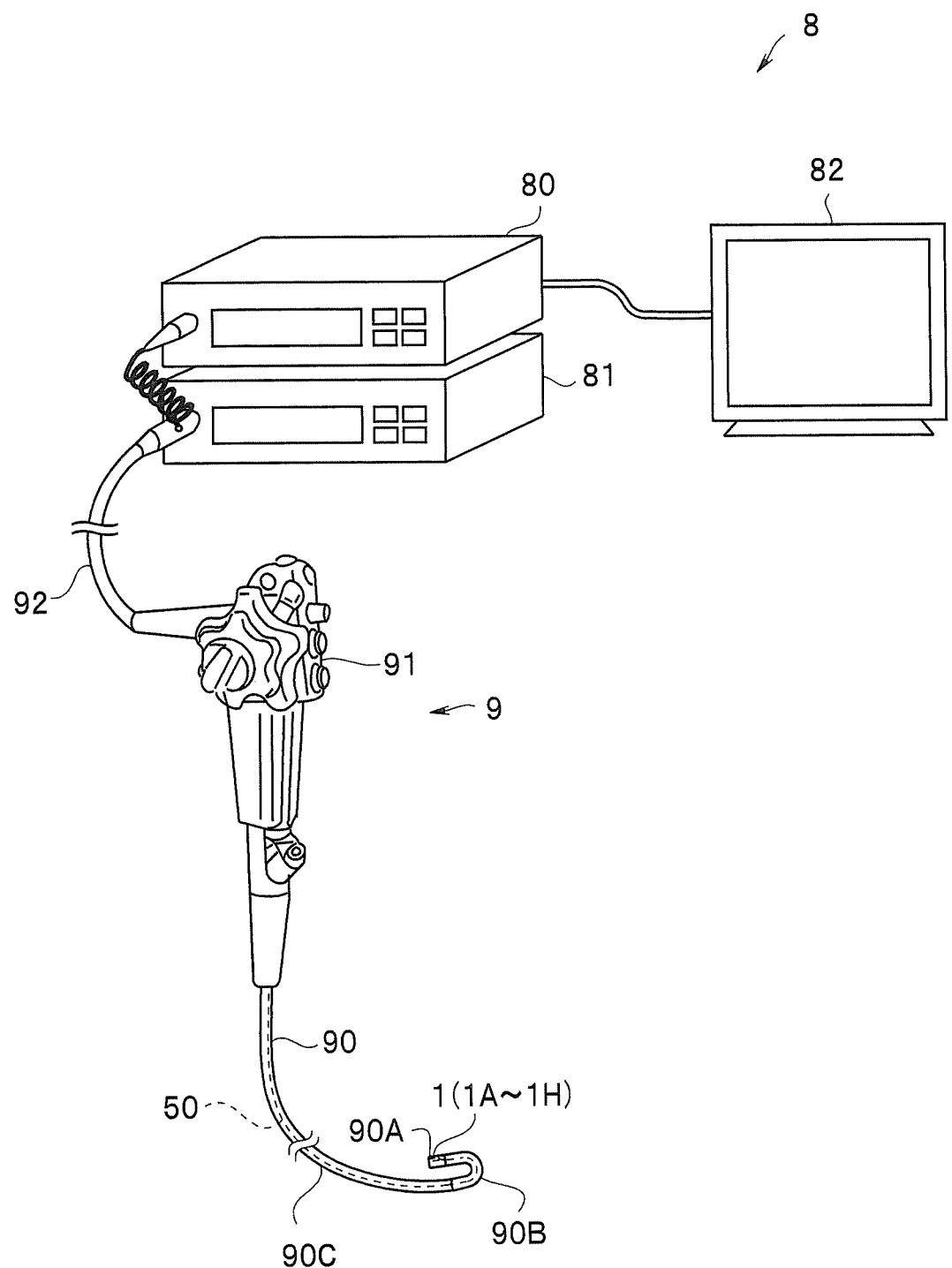
FIG. 1 is a perspective view of an endoscope system including an endoscope of a first embodiment.

As illustrated in FIG. 1, an endoscope system 8 including an endoscope 9 of the present embodiment includes the endoscope 9, a processor 80, a light source device 81, and a monitor 82. The endoscope 9 includes an insertion portion 90, an operation portion 91, and a universal cord 92. The insertion portion 90 is inserted into a body cavity of a subject, and the endoscope 9 photographs an in-vivo image of the subject and outputs an image signal.

Note that the endoscope 9 and the endoscope system 8 are described with a medical endoscope as an example below. However, it goes without saying that the present invention is also applicable to an industrial endoscope. Note that the industrial endoscope may be configured such that the insertion portion 90 and the monitor 82 are directly connected without interposing the operation portion 91 or the universal cord 92.

The insertion portion 90 is configured by a distal end portion 90A where an image pickup module 1 is disposed, a freely bendable bending portion 90B connected to a proximal end side of the distal end portion 90A, and a flexible portion 90C connected to a proximal end side of the bending portion 90B. The bending portion 90B is bent by an operation of the operation portion 91. Note that the endoscope 9 may be a rigid endoscope.

On a proximal end side of the insertion portion 90 of the endoscope 9, the operation portion 91 provided with various kinds of buttons configured to operate the endoscope 9 is disposed.

The light source device 81 includes a white LED, for example. Illumination light emitted by the light source device 81 is guided to the distal end portion 90A by a light guide (not illustrated) inserted through the universal cord 92 and the insertion portion 90, and illuminates the subject.

The endoscope 9 includes the insertion portion 90, the operation portion 91 and the universal cord 92, and transmits, by a signal cable 50 inserted through the insertion portion 90, an image pickup signal outputted by the image pickup module 1 disposed at the distal end portion 90A of the insertion portion 90. Since the image pickup module 1 is ultra-small, the distal end portion 90A of the insertion portion 90 has a narrow diameter and the endoscope 9 is lowly invasive.

Further, as described later, since the image pickup module 1 is small-sized, highly reliable and easy to manufacture, the endoscope 9 is lowly invasive, highly reliable and easy to manufacture.

Second Embodiment

Figure 2:
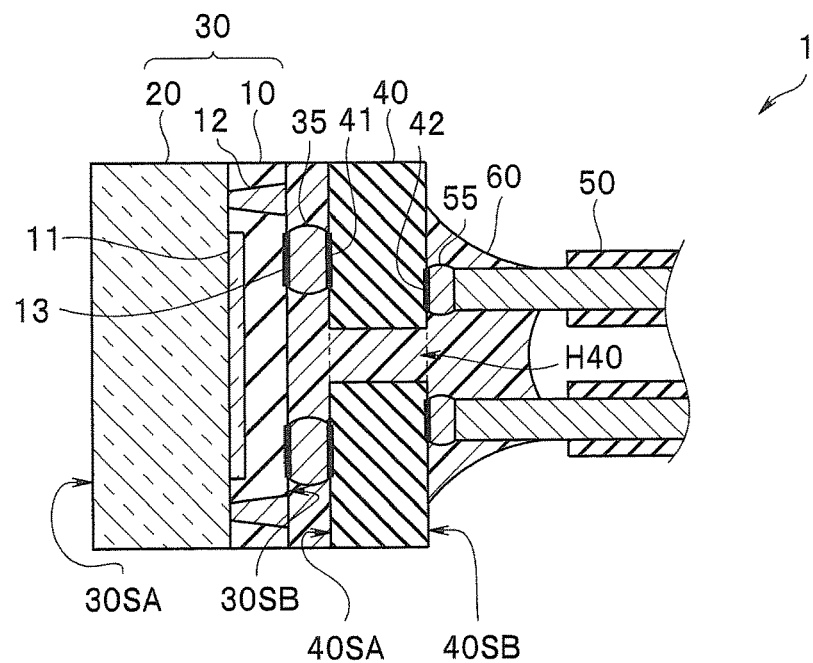
FIG. 2 is a sectional view of an image pickup module of a second embodiment.

As illustrated in FIG. 2, the image pickup module 1 includes an image pickup portion 30 that is an image pickup device, a wiring portion 40 that is a wiring element, the signal cable 50, and a first resin 60.

Note that in following description, it should be taken into consideration that drawings based on the respective embodiments are schematic and that a relation between a thickness and a width of respective parts and a ratio of the thicknesses of the respective parts or the like are different from the actual ones. Even between the drawings, a part where the relation of mutual dimensions or the ratio is different is sometimes included. In addition, illustrations and sign assignment of some components are sometimes omitted.

The image pickup portion 30 is an image pickup device 10 to which cover glass 20 is joined. The image pickup portion 30 includes a light receiving surface 30SA and a back surface 30SB opposite to the light receiving surface 30SA, and a plurality of external electrodes 13 are disposed on the back surface 30SB.

The image pickup device 10 is a CMOS (complementary metal oxide semiconductor) image sensor or a CCD (charge coupled device) or the like. The image pickup signal outputted by a light receiving portion 11 is transmitted to the external electrodes 13 by through wiring 12. In addition, the light receiving portion 11 receives drive power by different through wiring 12.

Figure 3:
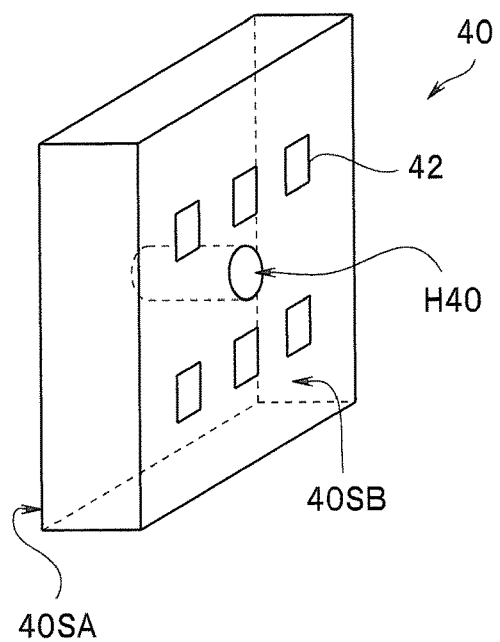
FIG. 3 is a perspective view of a wiring portion of the image pickup module of the second embodiment.

As illustrated in FIG. 3, the wiring portion 40 includes a first main surface 40SA and a second main surface 40SB opposite to the first main surface 40SA, and is formed of ceramic, glass, a resin, a fiber-reinforced resin, silicon, or the like.

A plurality of first electrodes 41 are disposed on the first main surface 40SA of the wiring portion 40 and a plurality of second electrodes 42 are disposed on the second main surface 40SB. The first electrode 41 is bonded with the external electrode 13 of the image pickup portion 30 by a first bump 35 which is a first bond portion. Note that the first electrode 41 may be bonded with the external electrode 13 of the image pickup portion 30 by solder or conductive resin paste. Further, a drive IC and a chip component such as a chip capacitor may be mounted on the wiring portion 40.

The wiring portion 40 is provided with a through-hole H40 passing through the first main surface 40SA and the second main surface 40SB.

The plurality of signal cables 50 supply the drive power (a drive signal) to the image pickup portion 30 and also transmit the image pickup signal. The signal cable 50 is bonded with the second electrode 42 on the second main surface 40SB of the wiring portion 40 by a second bump 55 which is a second bond portion. Note that the wiring portion 40 and the signal cable 50 may be bonded by the solder or the conductive resin paste.

The first resin 60 seals not only the second bump 55 which is the second bond portion but also the first bump 35 which is the first bond portion. In other words, an underfill resin sealing a gap between the image pickup portion 30 and the wiring portion 40 and a resin sealing a bond portion of the signal cable 50 and the wiring portion 40 are formed of the integrated same first resin 60.

The first resin 60 is a curable resin such as an epoxy resin or a silicone resin, is liquid before curing treatment, and is solidified when thermosetting treatment is performed after ultraviolet curing treatment, for example.

Figure 4:
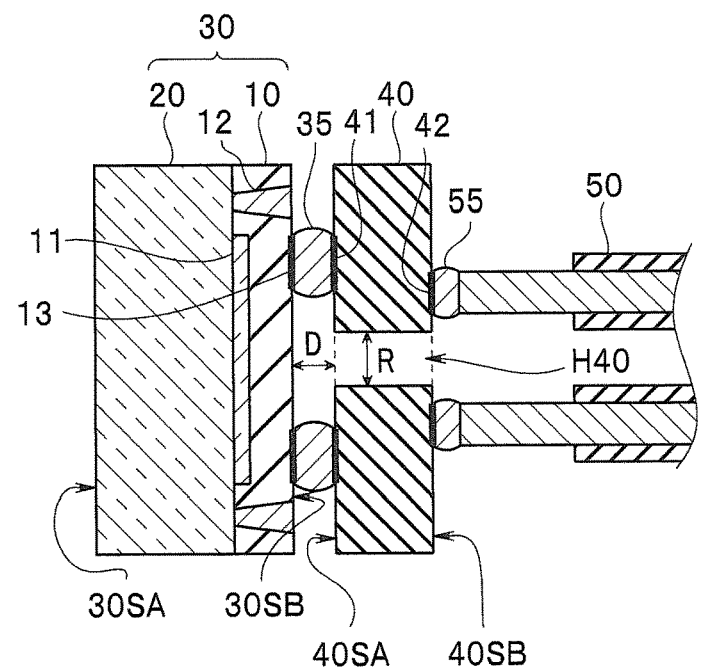
FIG. 4 is a sectional view for explaining a manufacturing method of the image pickup module of the second embodiment.
Figure 5:
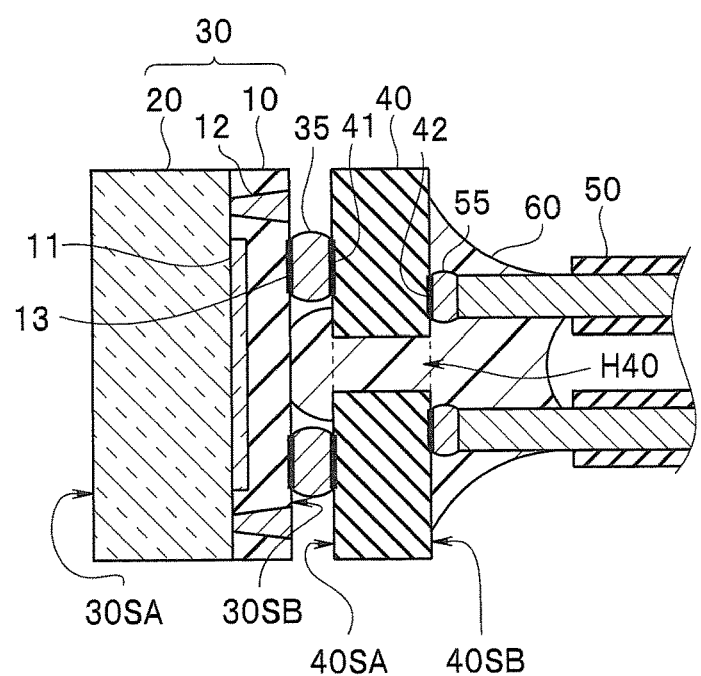
FIG. 5 is a sectional view for explaining the manufacturing method of the image pickup module of the second embodiment.

As illustrated in FIG. 5, the first resin 60 is disposed at the second bump 55 which is the second bond portion in a liquid state, passes through the through-hole H40 by a capillary phenomenon and spreads between the back surface 30SB of the image pickup portion 30 and the first main surface 40SA of the wiring portion 40. Note that FIG. 4 illustrates a state before the first resin 60 spreads. Then, the first resin 60 spreads around the first bump 35 so as to cover at least the first bump 35 which is the first bond portion, and is then cured. The first resin 60 around the second bump 55 enters the through-hole H40 of a small diameter by an action of surface tension. The first resin 60 that fills the through-hole H40 enters the gap between the back surface 30SB and the first main surface 40SA where the surface tension larger than the surface tension in the through-hole H40 acts, and spreads around the first bump 35. In other words, the first resin 60 fills the through-hole H40, and the first resin 60 reaches the first bump 35 by passing through the through-hole H40.

As illustrated in FIG. 5, in order for the liquid first resin 60 disposed to cover the second bump 55 on the second main surface 40SB to spread through the through-hole H40 to the first bump 35 by the capillary phenomenon, an interval D between the back surface 30SB of the image pickup portion 30 and the first main surface 40SA of the wiring portion 40 is set smaller than an inner diameter R which is an internal dimension of the through-hole H40.

It is preferable that the inner diameter R be 200 μm or smaller, and the interval D be 1 μm or larger and be 100 μm or smaller. It is particularly preferable that the inner diameter R be larger than 50 μm and be 100 μm or smaller, and the interval D be 5 μm or larger and be 30 μm or smaller.

When the inner diameter R of the through-hole H40 is the upper limit value or smaller, the liquid first resin 60 disposed on the second main surface 40SB is easily filled in the through-hole H40 by the capillary phenomenon. When the interval D is the lower limit value or larger, bond reliability of the first bond portion can be guaranteed. Since the interval D is smaller than the inner diameter R, the liquid first resin 60 filled in the through-hole H40 spreads between the back surface 30SB of the image pickup portion 30 and the first main surface 40SA of the wiring portion 40 by the capillary phenomenon, seals the first bump 35 as underfill, and also contributes to adhesion strength improvement between the image pickup portion 30 and the wiring portion 40.

By disposing the liquid first resin 60 in the state of covering the second bump 55 on the second main surface 40SB, the first resin 60 can also be filled between the image pickup portion 30 and the wiring portion 40 so that the image pickup module 1 is easy to manufacture and is highly reliable even though the image pickup module 1 is ultra-small.

Note that an opening (sectional shape) of the through-hole H40 is circular but the opening may be rectangular or polygonal. In a non-circular through-hole, by designing a maximum opening dimension as the internal dimension, underfilling can be performed by the capillary phenomenon. For example, in a case of the through-hole with a rectangular opening, a length of a diagonal line is designed as the internal dimension. In addition, the wiring portion 40 may be provided with the plurality of through-holes H40.

While the first bond portion and the second bond portion are both bond portions by bumps, at least one of the first bond portion and the second bond portion may be an ultrasound bond portion or a direct bond portion or the like.

Note that it cannot be specified by a structure that the image pickup module 1 of a finished product is manufactured by the above-described method utilizing the capillary phenomenon, and it is practically impossible to prove a manufacturing method by analysis. In other words, it is not practical to clarify by analysis whether the first resin sealing the first bond portion as the underfill is injected from a gap on a side face or is injected through the through-hole H40.

Modification 1 of Second Embodiment

Since an image pickup module 1A of the modification 1 of the second embodiment is similar to the image pickup module 1 of the second embodiment and has the same effects, the same signs are attached to the same components and description is omitted.

Figure 6:
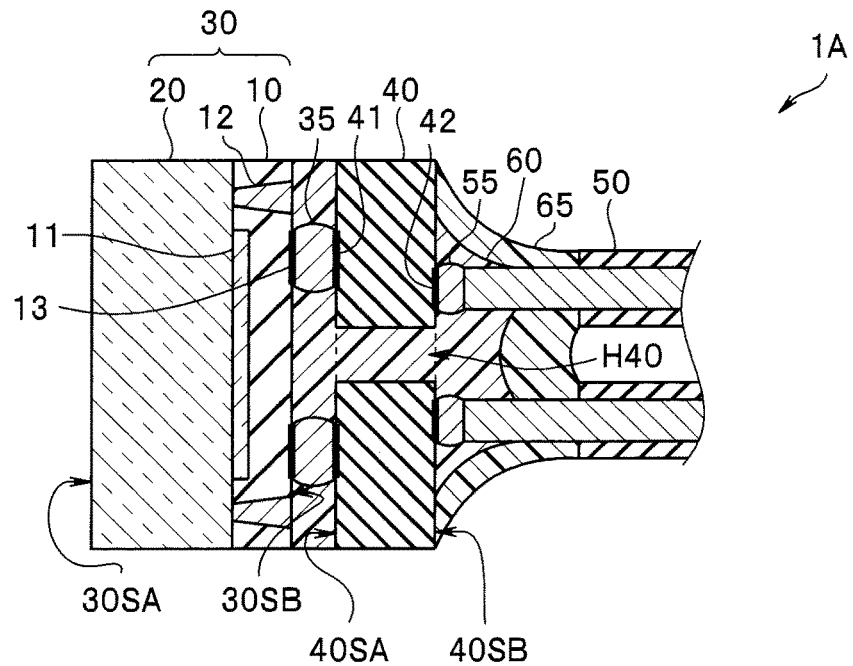
FIG. 6 is a sectional view of an image pickup module of a modification 1 of the second embodiment.

As illustrated in FIG. 6, the image pickup module 1A further includes a second resin 65 that covers a surface of the first resin 60 on the second main surface sealing the bump 55 which is the second bond portion of the first resin. A Young's modulus of the second resin 65 is smaller than a Young's modulus of the first resin 60.

For example, the first resin 60 is the epoxy resin, the Young's modulus of which is 5 GPa, and the second resin 65 is silicone rubber, the Young's modulus of which is 0.2 GPa.

When stress is applied to the signal cable 50, the stress is mitigated by the second resin 65 of the low Young's modulus. Therefore, the image pickup module 1A is more highly reliable than the image pickup module 1. The Young's modulus is measured by ASTM, D638, for example.

A kind of the first resin 60 or the second resin 65 is not limited in particular. However, it is preferable that the first resin be a thermosetting resin, the second resin be a thermoplastic resin, and the Young's modulus of the first resin be higher than the Young's modulus of the second resin. Examples of the thermosetting resin are a phenol resin (Young's modulus: 3 GPa-8 GPa), a urea resin (Young's modulus: 1 GPa-5 GPa), a melamine resin (Young's modulus: 5 GPa-15 GPa), the epoxy resin (Young's modulus: 3 GPa-10 GPa), the silicone resin (Young's modulus: 0.5 GPa-2 GPa), and a polyester resin (Young's modulus: 1 GPa-3 GPa). Examples of the thermoplastic resin are the silicone rubber (Young's modulus: 0.01 GPa-1 GPa) and an acrylic resin (0.01 GPa-1 GPa). Of course, the resin is not limited to the examples. In addition, fillers such as glass fibers or high thermal conductivity particles such as silicon particles may be added to the resin.

For example, in the case where the first resin 60 is the melamine resin, the epoxy resin, the Young's modulus of which is lower than the Young's modulus of the melamine resin, can be used as the second resin 65. In addition, even for the resin of the same group, when conditions described above are satisfied, the same material of a different Young's modulus may be used.

Note that since an effect is remarkable, it is preferable that the Young's modulus of the second resin 65 be 50% or lower of the Young's modulus of the first resin 60, and be particularly preferably 25% or lower.

Instead of the Young's modulus described above, as a material characteristic, a value of any one of tension, a compressive elastic modulus, and a bending elastic modulus may be substituted as a general term.

Third Embodiment

Since an image pickup module 1B of the third embodiment is similar to the image pickup module 1A of the second embodiment and has the same effects, the same signs are attached to the same components and the description is omitted.

Figure 7:
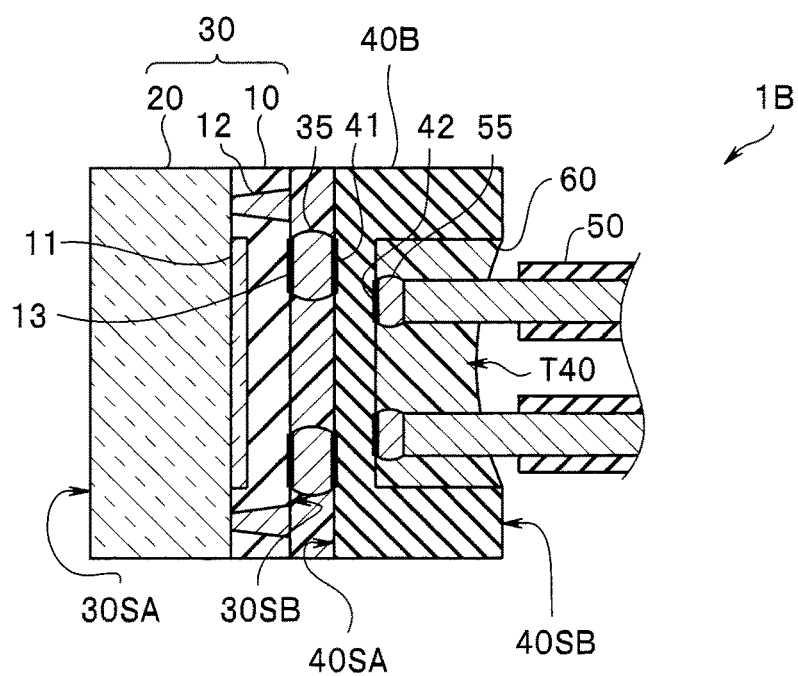
FIG. 7 is a sectional view of an image pickup module of a third embodiment.

As illustrated in FIG. 7, in the image pickup module 1B, a recessed portion T40 is provided on the second main surface 40SB of a wiring portion 40B, and the second electrodes 42 are disposed on a bottom surface of the recessed portion T40. The first resin 60 is disposed only in the recessed portion T40. Note that it is enough if the second electrodes 42 are disposed on the bottom surface or the side face which is an inner surface of the recessed portion T40.

Distal end portions of the plurality of signal cables 50 of the image pickup module 1B are surely sealed by the first resin 60 filled in the recessed portion T40, a depth of which is 500 μm, for example. In addition, since the first resin 60 does not project from the second main surface 40SB and spread to a rear portion, a length of a rigid portion is short.

Modifications of Third Embodiment

Since image pickup modules 1C-1F of modifications 1-4 of the third embodiment are similar to the image pickup module 1B of the third embodiment or the like and have the same effects, the same signs are attached to the same components and the description is omitted.

Modification 1 of Third Embodiment

Figure 8:
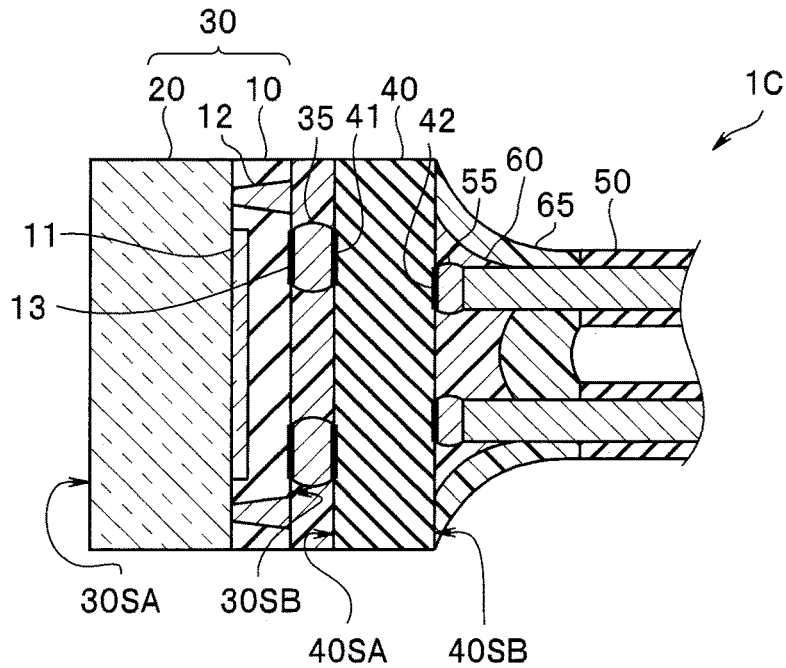
FIG. 8 is a sectional view of an image pickup module of a modification 1 of the third embodiment.

As illustrated in FIG. 8, the image pickup module 1C of the modification 1 of the third embodiment further includes the second resin 65 that covers the surface of the first resin 60. The Young's modulus of the second resin 65 is smaller than the Young's modulus of the first resin 60.

In the case where the stress is applied to the signal cable 50, the stress is mitigated by the second resin 65 of the low Young's modulus. Therefore, the image pickup module 1C is more highly reliable than the image pickup module 1.

Modification 2 of Third Embodiment

Figure 9:
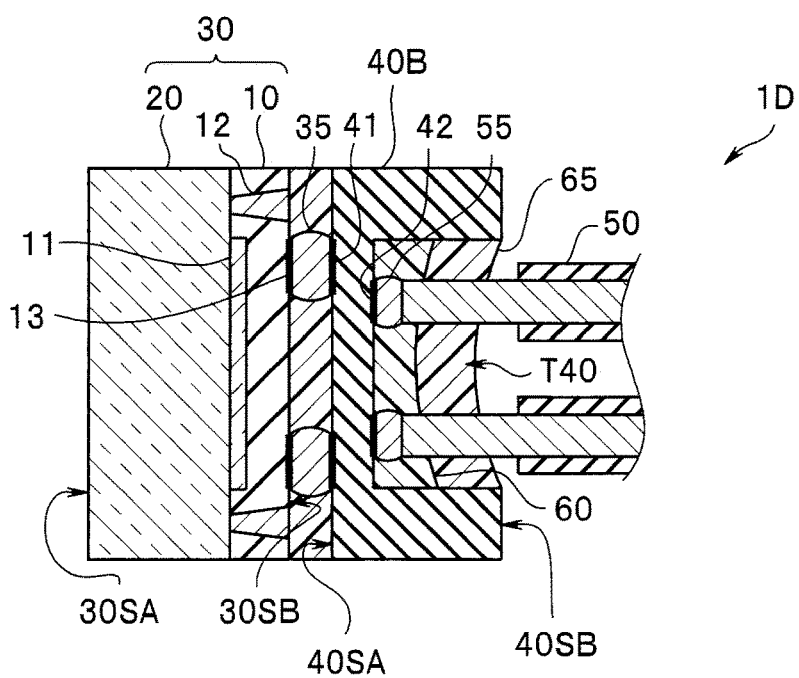
FIG. 9 is a sectional view of an image pickup module of a modification 2 of the third embodiment.

As illustrated in FIG. 9, in the image pickup module 1D of the modification 2 of the third embodiment, the recessed portion T40 is provided on the second main surface 40SB of the wiring portion 40B, and the second electrodes 42 are disposed on the bottom surface of the recessed portion T40. The first resin 60 is disposed only in the recessed portion T40.

The second resin 65 that covers the surface of the first resin 60 is further provided. The Young's modulus of the second resin 65 is smaller than the Young's modulus of the first resin 60.

The image pickup module 1D has the effect of the image pickup module 1B and the effect of the image pickup module 1C.

Modification 3 of Third Embodiment

Figure 10:
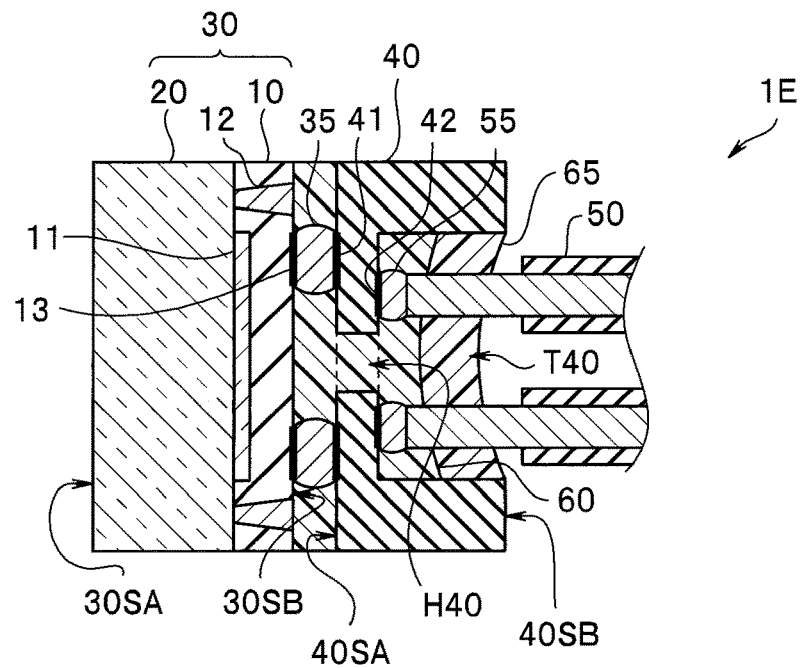
FIG. 10 is a sectional view of an image pickup module of a modification 3 of the third embodiment.

As illustrated in FIG. 10, the wiring portion 40 of the image pickup module 1E of the modification 3 of the third embodiment is provided with the through-hole H40 passing through the first main surface 40SA and the second main surface. Similarly to the image pickup module 1, the first resin 60 seals the first bump 35 which is the first bond portion and the second bump 55 which is the second bond portion, and is also filled in the through-hole H40.

The second resin 65 that covers the surface of the first resin 60 is further provided. The Young's modulus of the second resin 65 is smaller than the Young's modulus of the first resin 60. The second resin 65 is also disposed only in the recessed portion T40.

The image pickup module 1E has the effect of the image pickup module 1A and the effect of the image pickup module 1B.

Modification 4 of Third Embodiment

Figure 11:
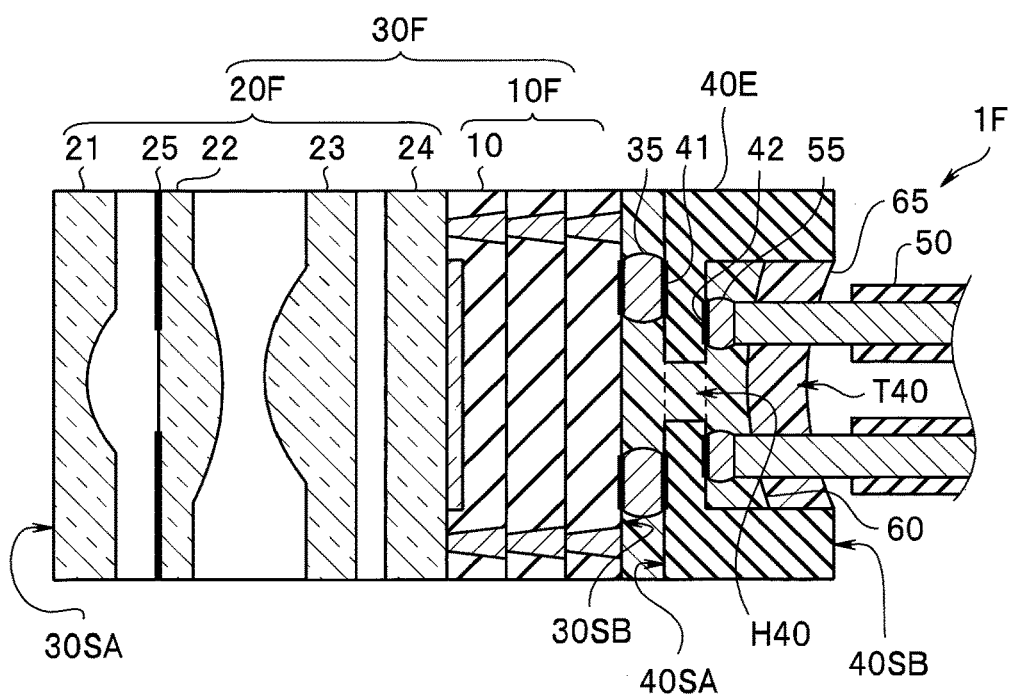
FIG. 11 is a sectional view of an image pickup module of a modification 4 of the third embodiment.

As illustrated in FIG. 11, in the image pickup module 1F of the modification 4 of the third embodiment, an image pickup portion 30F includes a lens unit 20F and a laminated element 10F.

The lens unit 20F is manufactured by cutting a laminated optical wafer in which a plurality of optical wafers are laminated so that the lens unit 20F is a rectangular parallelepiped. For example, the lens unit 20F includes lenses 21, 22 and 23, an infrared cut filter 24, and an aperture 25. The laminated element 10F is manufactured by cutting a laminated semiconductor wafer in which a plurality of semiconductor wafers including an image pickup wafer are laminated so that the laminated element 10F is a rectangular parallelepiped.

In other words, the image pickup portion of the image pickup module of the present invention may be configured only by the image pickup device, may be the image pickup device to which the cover glass is joined, or may be a laminated body of a plurality of elements including the image pickup device.

Fourth Embodiment

Since an image pickup module 1G of the fourth embodiment and an image pickup module 1H of a modification of the fourth embodiment are similar to the image pickup module 1 of the first embodiment and have the same effects, the same signs are attached to the same components and the description is omitted.

Figure 12:
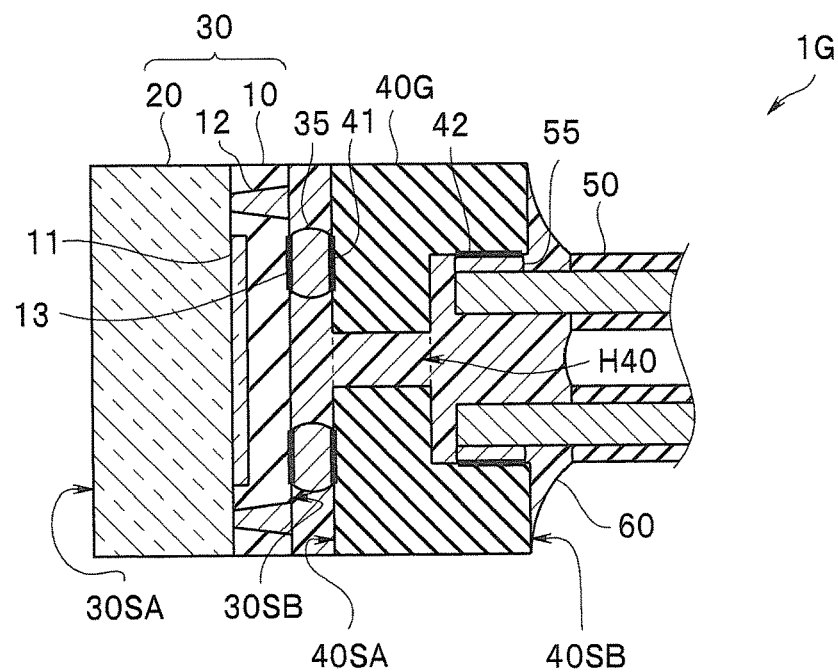
FIG. 12 is a sectional view of an image pickup module of a fourth embodiment.

As illustrated in FIG. 12, a step portion is provided on the second main surface 40SB of a wiring portion 40G of the image pickup module 1G, and the second electrodes 42 are disposed on the inner surface of the step portion.

Figure 13:
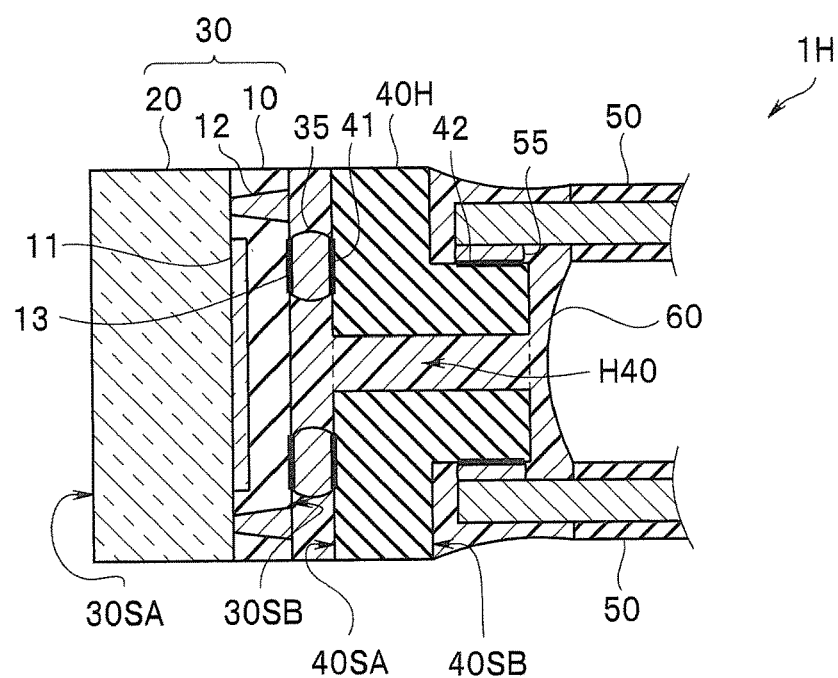
FIG. 13 is a sectional view of an image pickup module of a modification of the fourth embodiment.

As illustrated in FIG. 13, the step portion is also provided on the second main surface 40SB of a wiring portion 40H of the image pickup module 1H, and the second electrodes 42 are disposed on an outer surface of the step portion.

In other words, the second electrodes 42 may not be disposed on a surface parallel to the first main surface as long as the second electrodes 42 are disposed on a second main surface side.

Note that in the image pickup modules 1A-1F as well, the second electrodes 42 may not be disposed on the surface parallel to the first main surface as long as the second electrodes 42 are disposed on the second main surface side.

Needless to say, when the endoscope 9 of the first embodiment is provided with the image pickup modules 1A-1H, the endoscope 9 has the effects of the respective image pickup modules further in addition to the effect of the endoscope 9.

In other words, the present invention is not limited to the embodiments or the modifications described above, but can be variously changed and modified or the like without changing a subject matter of the present invention.

What is claimed is:

1. An endoscope comprising:
    an insertion portion; and
    an image pickup module configured to transmit, by a signal cable, an image pickup signal outputted by the image pickup module, the image pickup module being disposed at a distal end portion of the insertion portion,
    wherein the image pickup module comprises:
        an image sensor including a light receiving surface and a back surface, an external electrode being disposed on the back surface;
        a wiring substrate including a first main surface and a second main surface, the wiring substrate including a through-hole passing through the first main surface and the second main surface, a first electrode being disposed on the first main surface, a second electrode being disposed on the second main surface, a gap provided between the back surface of the image sensor and the first main surface of the wiring substrate in which the first electrode is bonded with the external electrode of the image sensor pickup device;

the signal cable is bonded with the second electrode of the wiring substrate; and a single integral first resin that fills the gap to surround a first bond portion bonding the first electrode and the external electrode, fills the through hole and seals a second bond portion bonding the second electrode and the signal cable.

2. The endoscope according to claim 1, wherein a first dimension of the gap between the back surface and the first main surface is smaller than an internal second dimension of the through-hole.

3. The endoscope according to claim 2, wherein the first dimension is 30 μm or smaller, and the internal second dimension is 100 μm or smaller.

4. The endoscope according to claim 1, wherein the first resin is a curable resin that is disposed at the second bond portion in a liquid state, spreads through the through-hole to the first bond portion by a capillary phenomenon, and seals the second bond portion and is then cured.

5. The endoscope according to claim 1, further comprising a second resin covering a surface of the first resin at the second bond portion, wherein a Young's modulus of the second resin is smaller than a Young's modulus of the first resin.

6. The endoscope according to claim 5, wherein a recess is provided on the second main surface of the wiring substrate, the second electrode is disposed on a bottom surface or a side face of the recessed portion, and the first resin and the second resin are disposed only in the recess.

* * * * *